United States Patent [19]
Greene et al.

[11] Patent Number: 6,107,075
[45] Date of Patent: *Aug. 22, 2000

[54] HUMAN ELASTASE IV

[75] Inventors: John M. Greene, Gaithersburg; Mark D. Adams, Potomac, both of Md.

[73] Assignee: Human Genome Sciences, Inc., Rockville, Md.

[*] Notice: This patent is subject to a terminal disclaimer.

[21] Appl. No.: 09/199,793

[22] Filed: Nov. 25, 1998

Related U.S. Application Data

[60] Division of application No. 08/765,192, filed as application No. PCT/US95/07236, Jun. 6, 1995, Pat. No. 5,851,814, which is a continuation-in-part of application No. 08/270,584, Jul. 5, 1994, Pat. No. 5,710,035.

[51] Int. Cl.$^7$ ............... C12Q 1/37; C12N 9/66; C12N 15/57; C12N 15/63; C12N 15/85

[52] U.S. Cl. ............ 435/218; 435/69.1; 435/23; 435/252.3; 435/320.1; 536/23.2

[58] Field of Search ........... 435/69.1, 23, 252.3, 435/320.1, 218; 536/23.2

[56] References Cited

U.S. PATENT DOCUMENTS

| | | | |
|---|---|---|---|
| 4,968,614 | 11/1990 | Takiguchi et al. | 435/218 |
| 4,985,361 | 1/1991 | Takiguchi et al. | 435/218 |
| 5,710,035 | 1/1998 | Greene et al. | 435/218 |
| 5,738,991 | 4/1998 | Braxton et al. | 435/6 |
| 5,851,814 | 12/1998 | Greene et al. | 435/218 |
| 5,856,109 | 1/1999 | Braxton et al. | 435/7.6 |
| 6,030,791 | 2/2000 | Braxton et al. | 435/7.1 |

FOREIGN PATENT DOCUMENTS

| | | |
|---|---|---|
| 157 604 | 10/1985 | European Pat. Off. |
| 198 645 | 10/1986 | European Pat. Off. |
| 0 768 378 | 1/1996 | European Pat. Off. |
| 61-11168 | 5/1986 | Japan |
| 96/00287 | 1/1996 | WIPO |

OTHER PUBLICATIONS

Largman et al. (1976) Biochem. 15(11):2491–2300.
Tomomura et al. (1995) J. Biol. Chem. 270(51)30315–30321.
Supplementary European Search Report, Application No. 95922998.0, dated Mar. 9, 1998.
Bowie et al. (1990) Science 247:1306–1310.
Kang et al. (1992) Gene 110(2):181–187.
Tomomura et al. (1996) FEBS Letts. 386:26–28.
Yoshino–Yasuda et al. (1998) J. Biochem. 123:45–554.

Primary Examiner—Ponnathapuca Achutamurthy
Assistant Examiner—William W. Moore
Attorney, Agent, or Firm—Human Genome Sciences, Inc.

[57] ABSTRACT

Human elastase IV polypeptides and DNA (RNA) encoding such polypeptides and a procedure for producing such polypeptide by recombinant techniques and utilizing such polypeptide for therapeutic purposes, for example, restoration of elasticity of arterial walls, improvement of serum lipid abnormality and improvement of serum lipoprotein metabolism are disclosed. Also disclosed are antagonist/inhibitors against such polypeptides and their use in treating inflammation, arthritis, e.g. rheumatoid arthritis and osteoarthritis, septic shock, pancreatitis and limiting tissue damage in ulceration. Diagnostic assays for identifying mutations in nucleic acid sequence encoding a polypeptide of the present invention and for detecting altered levels of the polypeptide of the present invention are also disclosed.

35 Claims, 2 Drawing Sheets

```
  1  ATGTTGGGCA TCACTGTCCT CGCTGCGCTC TTGGCCTGTG
        M  L  G  I  T  V  L  A  A  L  L  A  C
 41  CCTCCAGCTG TGGGGTGCCC AGCTTCCCGC CCAACCTATC
        A  S  S  C  G  V  P  S  F  P  P  N  L  S
 81  CGCCCGAGTG GTGGGAGGAG AGGATGCCCG GCCCCACAGC
        A  R  V  V  G  G  E  D  A  R  P  H  S
121  TGGCCCTGGC AGATCTCCCT CCAGTACCTC AAGAACGACA
        W  P  W  Q  I  S  L  Q  Y  L  K  N  D
161  CGTGGAGGCA TACGTGTGCC GGGACTTTGA TTGCTAGCAA
        T  W  R  H  T  C  G  T  L  I  A  S  N
201  CTTCGTCCTC ACTGCCGCCC ACTGCATCAG CAACACCCGG
        F  V  L  T  A  A  H  C  I  S  N  T  R
241  ACCTACCGTG TGGCCGTGGG AAAGAACAAC CTGGAGGTGG
        T  Y  R  V  A  V  G  K  N  N  L  E  V
281  AAGACGAAGA AGGATCCCTG TTTGTGGGTG TGGACACCAT
        E  D  E  E  G  S  L  F  V  G  V  D  T  I
321  CCACGTCCAC AAGAGATGGA ATGCCCTCCT GTTGCGCAAT
        H  V  H  K  R  W  N  A  L  L  R  N
361  GATATTGCCC TCATCAAGCT TGCAGAGCAT GTGGAGCTGA
        D  I  A  L  I  K  L  A  E  H  V  E  L
401  GTGACACCAT CCAGGTGGCC TGCCTGCCAG AGAAGGACTC
        S  D  T  I  Q  V  A  C  L  P  E  K  D  S
441  CCTGCTCCCC AAGGACTACC CCTGCTATGT CACCGGCTGG
        L  L  P  K  D  Y  P  C  Y  V  T  G  W
481  GGCCGCCTCT GGACCAACGG CCCCATTGCT GATAAGCTGC
        G  R  L  W  T  N  G  P  I  A  D  K  L
521  AGCAGGGCCT GCAGCCGGTG GTGGATCACG CCAGGTGCTC
        Q  Q  G  L  Q  P  V  V  D  H  A  T  C  S
561  CAGGATTGAC TGGTGGGGCT TCAGGGTGAA GAAAACCATG
        R  I  D  W  W  G  F  R  V  K  K  T  M
601  GTGTGTGCGGTG GGGGGGATGG CGTCATCTCA GCCTGCAATG
        V  C  A  G  G  D  G  V  I  S  A  C  N
641  GGGACTCCGG TGGCCCACTG AACTGCCAGT TGGAGAACGG
        G  D  S  G  G  P  L  N  C  Q  L  E  N  G

681  TTCCTGGGAG GTGTTTGGCA TCGTCAGCTT TGGCTCCCGG
        S  W  E  V  F  G  I  V  S  F  G  S  R
721  CGGGGCTGCA ACACCCGCAA GAAGCCGGTA GTCTACACCC
        R  G  C  N  T  R  K  P  V  V  Y  T
761  GGGTGTCCGC CTACATCGAC TGGATCAACG AGAAAATGCA
        R  V  S  A  Y  I  D  W  I  N  E  K  M  Q
801  GCTGTGA
        L
```

| | |
|---|---|
| 1 | ATGTTGGGCA TCACTGTCCT CGCTGCGCTC TTGGCCTGTG |
| | M   L   G   I   T   V   L   A   A   L   L   A   C |
| 41 | CCTCCAGCTG TGGGGTGCCC AGCTTCCCGC CCAACCTATC |
| | A   S   S   C   G   V   P   S   F   P   P   N   L   S |
| 81 | CGCCCGAGTG GTGGGAGGAG AGGATGCCCG GCCCCACAGC |
| | A   R   V   V   G   G   E   D   A   R   P   H   S |
| 121 | TGGCCCTGGC AGATCTCCCT CCAGTACCTC AAGAACGACA |
| | W   P   W   Q   I   S   L   Q   Y   L   K   N   D |
| 161 | CGTGGAGGCA TACGTGTGGC GGGACTTTGA TTGCTAGCAA |
| | T   W   R   H   T   C   G   T   L   I   A   S   N |
| 201 | CTTCGTCCTC ACTGCCGCCC ACTGCATCAG CAACACCCGG |
| | F   V   L   T   A   A   H   C   I   S   N   T   R |
| 241 | ACCTACCGTG TGGCCGTGGG AAAGAACAAC CTGGAGGTGG |
| | T   Y   R   V   A   V   G   K   N   N   L   E   V |
| 281 | AAGACGAAGA AGGATCCCTG TTTGTGGGTG TGGACACCAT |
| | E   D   E   E   G   S   L   F   V   G   V   D   T   I |
| 321 | CCACGTCCAC AAGAGATGGA ATGCCCTCCT GTTGCGCAAT |
| | H   V   H   K   R   W   N   A   L   L   R   N |
| 361 | GATATTGCCC TCATCAAGCT TGCAGAGCAT GTGGAGCTGA |
| | D   I   A   L   I   K   L   A   E   H   V   E   L |
| 401 | GTGACACCAT CCAGGTGGCC TGCCTGCCAG AGAAGGACTC |
| | S   D   T   I   Q   V   A   C   L   P   E   K   D   S |
| 441 | CCTGCTCCCC AAGGACTACC CCTGCTATGT CACCGGCTGG |
| | L   L   P   K   D   Y   P   C   Y   V   T   G   W |
| 481 | GGCCGCCTCT GGACCAACGG CCCCATTGCT GATAAGCTGC |
| | G   R   L   W   T   N   G   P   I   A   D   K   L |
| 521 | AGCAGGGCCT GCAGCCCGTG GTGGATCACG CCACGTGCTC |
| | Q   Q   G   L   Q   P   V   V   D   H   A   T   C   S |
| 561 | CAGGATTGAC TGGTGGGGCT TCAGGGTGAA GAAAACCATG |
| | R   I   D   W   W   G   F   R   V   K   K   T   M |
| 601 | GTGTGCGCTG GGGGGGATGG CGTCATCTCA GCCTGCAATG |
| | V   C   A   G   D   G   V   I   S   A   C   N |
| 641 | GGGACTCCGG TGGCCCACTG AACTGCCAGT TGGAGAACGG |
| | G   D   S   G   G   P   L   N   C   Q   L   E   N   G |

Figure 1A

```
681  TTCCTGGGAG GTGTTTGGCA TCGTCAGCTT TGGCTCCCGG
      S  W  E   V  F  G  I   V  S  F   G  S  R
721  CGGGGCTGCA ACACCCGCAA GAAGCCGGTA GTCTACACCC
      R  G  C   N  T  R  K   K  P  V   V  Y  T
761  GGGTGTCCGC CTACATCGAC TGGATCAACG AGAAAATGCA
      R  V  S   A  Y  I  D   W  I  N   E  K  M  Q
801  GCTGTGA
      L
```

Figure 1B

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 807 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

-continued

```
ATGTTGGGCA TCACTGTCCT CGCTGCGCTC TTGGCCTGTG CCTCCAGCTG TGGGGTGCCC      60
AGCTTCCCGC CCAACCTATC CGCCCGAGTG GTGGGAGGAG AGGATGCCCG GCCCCACAGC     120
TGGCCCTGGC AGATCTCCCT CCAGTACCTC AAGAACGACA CGTGGAGGCA TACGTGTGGC     180
GGGACTTTGA TTGCTAGCAA CTTCGTCCTC ACTGCCGCCC ACTGCATCAG CAACACCCGG     240
ACCTACCGTG TGGCCGTGGG AAAGAACAAC CTGGAGGTGG AAGACGAAGA AGGATCCCTG     300
TTTGTGGGTG TGGACACCAT CCACGTCCAC AAGAGATGGA ATGCCCTCCT GTTGCGCAAT     360
GATATTGCCC TCATCAAGCT TGCAGAGCAT GTGGAGCTGA GTGACACCAT CCAGGTGGCC     420
TGCCTGCCAG AGAAGGACTC CCTGCTCCCC AAGGACTACC CCTGCTATGT CACCGGCTGG     480
GGCCGCCTCT GGACCAACGG CCCCATTGCT GATAAGCTGC AGCAGGGCCT GCAGCCCGTG     540
GTGGATCACG CCACGTGCTC CAGGATTGAC TGGTGGGGCT TCAGGGTGAA GAAAACCATG     600
GTGTGCGCTG GGGGGGATGG CGTCATCTCA GCCTGCAATG GGGACTCCGG TGGCCCACTG     660
AACTGCCAGT TGGAGAACGG TTCCTGGGAG GTGTTTGGCA TCGTCAGCTT TGGCTCCCGG     720
CGGGGCTGCA ACACCCGCAA GAAGCCGGTA GTCTACACCC GGGTGTCCGC CTACATCGAC     780
TGGATCAACG AGAAAATGCA GCTGTGA                                         807
```

(2) INFORMATION FOR SEQ ID NO:2:

(i) SEQUENCE CHARACTERISTICS:
        (A) LENGTH: 268 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Leu Gly Ile Thr Val Leu Ala Ala Leu Leu Ala Cys Ala Ser Ser
 1               5                  10                  15

Cys Gly Val Pro Ser Phe Pro Pro Asn Leu Ser Ala Arg Val Val Gly
                20                  25                  30

Gly Glu Asp Ala Arg Pro His Ser Trp Pro Trp Gln Ile Ser Leu Gln
            35                  40                  45

Tyr Leu Lys Asn Asp Thr Trp Arg His Thr Cys Gly Gly Thr Leu Ile
        50                  55                  60

Ala Ser Asn Phe Val Leu Thr Ala Ala His Cys Ile Ser Asn Thr Arg
65                  70                  75                  80

Thr Tyr Arg Val Ala Val Gly Lys Asn Asn Leu Glu Val Glu Asp Glu
                85                  90                  95

Glu Gly Ser Leu Phe Val Gly Val Asp Thr Ile His Val His Lys Arg
            100                 105                 110

Trp Asn Ala Leu Leu Leu Arg Asn Asp Ile Ala Leu Ile Lys Leu Ala
        115                 120                 125

Glu His Val Glu Leu Ser Asp Thr Ile Gln Val Ala Cys Leu Pro Glu
    130                 135                 140

Lys Asp Ser Leu Leu Pro Lys Asp Tyr Pro Cys Tyr Val Thr Glu Trp
145                 150                 155                 160

Glu Arg Leu Trp Thr Asn Glu Pro Ile Ala Asp Lys Leu Gln Gln Gly
                165                 170                 175

Leu Gln Pro Val Val Asp His Ala Thr Cys Ser Arg Ile Asp Trp Trp
            180                 185                 190
```

```
Gly Phe Arg Val Lys Lys Thr Met Val Cys Ala Gly Gly Asp Gly Val
            195                 200                 205

Ile Ser Ala Cys Asn Gly Asp Ser Gly Gly Pro Leu Asn Cys Gln Leu
        210                 215                 220

Glu Asn Gly Ser Trp Glu Val Phe Gly Ile Val Ser Phe Gly Ser Arg
225                 230                 235                 240

Arg Gly Cys Asn Thr Arg Lys Lys Pro Val Val Tyr Thr Arg Val Ser
                245                 250                 255

Ala Tyr Ile Asp Trp Ile Asn Glu Lys Met Gln Leu
                260                 265
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCCAGAGTCG ACGTGGTGGG AGGAGAGGAT GCC        33

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GATCTTCTAG AATCACAGCT GCATTTTCTC GTTGAT        36

HUMAN ELASTASE IV

This application is a divisional of application Ser. No. 08/765,192, filed Apr. 24, 1997, now U.S. Pat. No. 5,851,814, which claims priority to PCT/US95/107236, filed Jun. 6, 1995, and which is a CIP of application Ser. No. 08/270,584, filed Jul. 5, 1994, now U.S. Pat. 5,710,035.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Human Elastase IV, sometimes hereinafter referred to as "HE IV". The invention also relates to inhibiting the action of such polypeptides.

Elastase is a serine protease, capable of hydrolyzing the fibrous insoluble protein known as elastin. Elastin is a scleroprotein forming connective tissues, tendons, aortic integuments and cervical bundles of higher animals. Elastin is only slightly degraded by other proteases such as pepsin and trypsin.

During the course of study on arteriosclerosis, Balo, et al. observed degradation of the elastin fibers of arterial walls, and postulated the presence of a degrading enzyme (Schweiz, Z., Pathol. Bacteriol., 12:350 (1949)). Subsequently, in 1952, Banga discovered an enzyme in the pancreas which specifically hydrolyses elastin. The enzyme was isolated in the form of crystals and named elastase (Acta. Physiol. Acad. Sci. Hung, 3:317 (1952).

Elastase has been confirmed to exist in the pancreas of most mammals, including humans, monkeys, cats, rabbits etc. A correlation is recognized between elastase activity in the age of a human being, a marked lowering in elastase activity in the pancreas and plasma of males over 40 and of females over 60 years has been reported by Loeven and Baldwin, Gerontologia, 17:170 (1971).

In the case of patients with arteriosclerosis, the elastase activity in the pancreas was reported by Balo and Banga to be markedly lower than that of healthy people, and in some cases it had completely disappeared (Nature, 178:310 (1956)). Subsequent studies have also demonstrated that elastase not only catalyses the hydrolysis of elastin but also accelerates elastin biosynthesis.

With the administration of porcine elastase to human beings, there is the risk of antibody formation due to the antigenic effect of the foreign protein. There is then the danger of anaphylaxis with repeated administration. Accordingly, human elastase is preferable for human use. However, it is extremely difficult to procure human elastase in sufficient quantities from the traditional source, the human pancreas.

In accordance with one aspect of the present invention, there is provided a novel mature polypeptide which is HE IV, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there is provided a process for utilizing such polypeptide, or polynucleotide encoding such polypeptide for therapeutic purposes, for example, restoring arterial wall elasticity, reducing serum lipid levels and improving lipoprotein metabolism.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of in the treatment of inflammation, arthritis, e.g. rheumatoid arthritis and osteoarthritis, septic shock, pancreatitis and limit tissue damage in ulceration.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

The following drawings are illustrative of embodiments of the invention and are not meant to limit thescope of the invention as encompassed by the claims.

FIG. 1 displays the cDNA sequence and corresponding deduced amino acid sequence for HE IV. The standard one letter abbreviation for amino acids is used.

In accordance with an aspect of the present invention, there is provided an isolated nucleic acid (polynucleotide) which encodes for the putative mature polypeptide having the deduced amino acid sequence of FIG. 1 (SEQ ID NO:2) or for the mature polypeptide encoded by the cDNA of the clone deposited as ATCC Deposit No. 75751 on Apr. 25, 1994.

The polynucleotide of this invention was discovered in a cDNA library derived from a human pancreas. It is structurally related to the serine protease family. It contains an open reading frame encoding a protein of about 268 amino acid residues of which approximately the first 16 amino acids residues are the putative leader sequence and amino acid 17–29 represent a prosequence such that the mature protein comprises 239 amino acids. The protein exhibits the highest degree of homology to rat Elastase IV with 72% identity and 82% a similarity over the entire amino acid sequence. The polynucleotide of this invention also has a high degree of homology to other elastase polypeptides and has two conserved motifs found in all serine proteases corresponding to the active site, namely LTAAHC at amino acids 76–81 and GDSGG at amino acids 219–223.

The polynuclectide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or noncoding sequence 5' and/or 3'0 of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a nonnaturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least so bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112.

The sequence of the polynucleotides contained in the deposited materials, as well as the amino acid sequence of the polypeprides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence rs) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,*

*Streptomyces, Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryo tic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting Transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

HE IV of the present invention may inhibit deposition of lipids and calcium on arterial walls, remove cholesterol and calcium from arterial walls, selectively degrade denatured elastin, accelerate synthesis of elastin fiber in arterial walls, lower serum lipids and improve lipoprotein metabolism. These capabilities lead to restoration of elasticity of arterial walls, improvement of serum lipid abnormality and improvement of serum lipoprotein metabolism, which are all positive for the reduction of cholesterol blockage of arteries.

The genetically engineered product can eliminate the dependency on human pancreas supplies for the elastase and avoids antibody formation and possibility of anaphylaxis using porcine elastase.

The HE IV polypeptides of the present invention also has a bio-industrial application, namely the enzyme may be used in laundry detergents.

The present invention is also directed to antagonist molecules of the polypeptides of the present invention, and their use in reducing or eliminating the function of the polypeptide.

An example of an antagonist is an antibody or in some cases, an oligonucleotide which binds to the polypeptide. Alternatively, antagonists to the polypeptides of the present invention may be employed which bind to the substrates to which a polypeptide of the present invention normally binds. The antagonists may be closely related proteins such that they recognize and bind to the substrate of the natural protein, however, they are inactive forms of the polypeptide and thereby prevent the action of Elastase IV since the substrate sites are blocked.

An example of an inhibitor is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (19 88); and Dervan et al., Science, 251: 1360 (1991)), thereby preventing transcription and the production of Elastase IV. The antisense RNA oligonucleotide hybridizes to the mRNA in vivo and blocks translation of the mRNA molecule into the Elastase IV (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of Elastase IV.

Another example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

The antagonists may be employed to treat inflammation, arthritis, e.g. rheumatoid arthritis and osteoarthritis, septic shock, pancreatitis and to limit tissue damage in ulceration. The antagonists may be employed in a composition with a pharmaceutically acceptable carrier, e.g., as hereinabove described.

The present invention also relates to an assay for identifying potential antagonists specific to HE IV. An example of such an assay combines purified HE IV and a potential antagonist/inhibitor in the presence of elastin under appropriate conditions for a competitive assay. Elastin can be labeled, such as by radio activity, such that the number of elastin molecules broken down by HE IV could be measured and the effectiveness of the potential antagonist could be determined.

The polypeptides of the present invention and antagonists may be employed in combination with a suitable pharmaceutical carrier. Such compositions comprise a therapeutically effective amount of the polypeptide or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or antagonists of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. Elastase IV may also be given orally to correct elastase deficiency. The amounts and dosage regimens of HE IV and administered to a subject will depend on a number of factors such as the mode of administration, the nature of the condition being treated and the judgment of the prescribing physician. Generally speaking, they are given, for example, in therapeutically effective doses of at least about 10 µg/kg body weight and in most cases they will be administered in an amount not in excess of about 8 mg/Kg body weight per day and preferably the dosage is from about 10 µg/kg to about 1 mg/kg body weight daily, taking into account the routes of administration, symptoms, etc.

The polypeptides or antagonists which are polypeptides may also be employed in accordance with the present invention by expression of such polype ptides in vivo, which is often referred to as "gene therapy."

Thus, for example, cells from a patient may be engineered with a polynucleotide (DNA or RNA) encoding HE IV ex viva, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in viva for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in viva after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of the polypeptide of the present invention.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and Sl protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the HE IV antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any HE IV proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to HE IV. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled HE IV and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic. oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

Example 1
Bacterial Expression and Purification of HE IV

The DNA sequence encoding for HE IV, ATCC # 75751 is initially amplified using PCR oligonucleotide primers corresponding to the 5' and sequences of the processed HE IV protein (minus the signal and activation peptide sequences) and the protein sequences at the 3' end of the HE IV gene. The 5' oligonucleotide primer has the sequence 5' GCCAGAGTCGACGTGGTGGGAGGAGAGGATGCC 3' (SEQ ID NO:3) and contains a SalI restriction enzyme site followed by 21 nucleotides of HE IV coding sequence starting from the presumed terminal amino acid of the processed protein codon. The 3' oligonucleotide primer 5' GATCTTCTAGAATCACAGCTGCATTTTCTCGTTGAT 3' (SEQ ID NO:4) contains complementary sequences to the XbaI restriction enzyme site and is followed by 24 nucleotides of the HE IV sequence. The restriction enzyme sites are compatible with restriction enzyme sites on the bacterial expression vector pQE-9 (Qiagen, Inc. 9259 Eton Avenue, Chatsworth, Calif., 91311). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 is then digested with SalI and XbaI. The amplified sequences are ligated into pQE-9 after digestion with SalI and XbaI and are inserted in frame with the sequence encoding for the histidine tag and the RBS (see FIG. 3). The ligation mixture was then used to transform E. coli strain available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$_{600}$) of between 0.4 and 0.6. IPTG ("Isopropyl-b-D thiogalacto pyranoside") is then added to a final concentration of 1 mM. IPTG induces the HE IV gene by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized HE IV was purified from this solution by chromatography on a Nickel-Chelate column under conditions that allow for tight binding of proteins containing the 6-His tag (Hochuli, E. et al., J. Chromatography 411:177–184 (1984)). HE IV is eluted from the column in 6 Molar Guanidine HCl, 100 mM sodium phosphate, 10 mM glutathione (reduced), and 2 mM glutathione (oxidized). After incubation in this solution for 12 hours the protein was dialyzed to 10 mM sodium phosphate.

Example 2
Expression of HE IV by in vitro Transcription and Translation

The in vitro transcription and translation of HE IV was carried out using the TNT Coupled Reticulocyte Lysate System (Promega, 2800 Woods Hollow Road, Madison, Wis. 53771–5399). The cDNA encoding for HE IV, ATCC # 75751, was cloned directionally EcoRI to XhoI with the EcoRI site defining the 5' end of the gene and the XhoI site defining the 3' end of the gene. The gene was inserted in the T3 direction. T3 defines a bacteriophage RNA polymerase which recognizes a specific promoter, and transcribes the DNA into a mRNA. A rabbit reticulocyte lysate is supplemented with T3 RNA polymerase and directs the expression of proteins with a T3 promoter utilizing the T3 RNA polymerase to transcribe the message, and the reticulocyte lysate to translate the nascent RNA. 1 µg of plasmid containing the HE IV DNA was incubated at 30° C. for 1 hour with the reticulocyte lysate, T3 RNA polymerase and [$^{35}$S]-Methionine. After incubation, the translation product was separated by 10% SDS-PAGE gel electrophoresis. The gel was fixed in 10% acetic acid, 15% methanol for 30 minutes followed by drying on a Bio-Rad gel dryer for one hour. Autoradiography was carried out with Kodak XAR film. The film was exposed at −80° C. with intensifying screen.

Example 3
Expression Pattern of HE IV in Human Tissue

Northern blot analysis was carried out to examine the levels of expression of HE IV in human tissues. Total cellular RNA samples were isolated with RNAzol™ B system (Biotecx Laboratories, Inc. 6023 South Loop East, Houston, Tex. 77033). About 10 μg of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime–3 Prime, Inc. 5603 Arapahoe Road, Boulder, Colo. 80303). The filter was then hybridized with radioactive labeled full length HE IV gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for HE IV is abundant only in the pancreas.

Example 4
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P.T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cell now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid encoding a polypeptide selected from the group consisting of:
   (a) a polypeptide consisting of amino acids 1 to 268 of SEQ ID NO:2;
   (b) a polypeptide consisting of a mino acids 2 to 268 of SEQ ID NO:2;
   (c) a polypeptide consisting of amino acids 16 to 268 in SEQ ID NO:2;
   (d) a polypeptide consisting of amino acids 30 to 268 in SEQ ID NO:2;
   (e) a polypeptide having protease activity consisting of amino acids 30 to 268 of SEQ ID NO:2, except for at least one conservative amino acid substitution;
   (f) a fragment of the polypeptide of (a) having protease activity; and
   (g) a fragment of the polypeptide of (a) which binds to an antibody specific for the polypeptide of (a).

2. The isolated polynucleotide of claim 1 wherein said polypeptide is (a).

3. The isolated polynucleotide of claim 1 wherein said polypeptide is (b).

4. The isolated polynucleotide of claim 1 wherein said polypeptide is (c).

5. The isolated polynucleotide of claim 1 wherein said polypeptide is (d).

6. The isolated polynucleotide of claim 1 wherein said polypeptide is (e).

7. The isolated polynucleotide of claim 1 wherein said polypeptide is (f).

8. The isolated polynucleotide of claim 1 wherein said polypeptide is (g).

9. An isolated polynucleotide comprising a nucleic acid encoding a polypeptide selected from the group consisting of:
   (a) the full-length polypeptide encoded by the human cDNA contained in ATCC Deposit No. 75751;
   (b) the full-length polypeptide encoded by the human cDNA contained in ATCC Deposit No. 75751, excepting the N-terminal methionine;
   (c) the mature polypeptide encoded by the human cDNA contained in ATCC Deposit No. 75751 ;
   (d) a polypeptide having protease activity consisting of the amino acid sequence of the polypeptide of (c), except for at least one conservative amino acid substitution;
   (e) a fragment of the polypeptide of (a) having protease activity; and
   (f) a fragment of the polypeptide of (a) which binds an antibody specific for the polypeptide of (a).

10. The isolated polynucleotide of claim 9 wherein said polypeptide is (a).

11. The isolated polynucleotide of claim 9 wherein said polypeptide is (b).

12. The isolated polynucleotide of claim 9 wherein said polypeptide is (c).

13. The isolated polynucleotide of claim 9 wherein said polypeptide is (d).

14. The isolated polynucleotide of claim 9 wherein said polypeptide is (e).

15. The isolated polynucleotide of claim 9 wherein said polypeptide is (f).

16. An isolated polynucleotide comprising a nucleic acid that hybridizes to a polynucleotide consisting of SEQ ID NO:1, the complement thereof, or The cDNA contained in ATCC Deposit No. 755751 under hybridization conditions comprising hybridization in a wash buffer consisting of 0.5×SSC and 0.1% SDS at 60° C.

17. An isolated polynucleotide complementary to the nucleic acid of claim 1.

18. An isolated polynucleotide complementary to the nucleic acid of claim 9.

19. An isolated polynucleotide complementary to the nucleic acid of claim 16.

20. The isolated polynucleotide of claim 1, wherein said nucleic acid is linked to a heterologous polynucleotide.

21. The isolated polynucleotide of claim 9, wherein said nucleic acid is linked to a heterologous polynucleotide.

22. The isolated polynucleotide of claim 16, wherein said nucleic acid is linked to a heterologous polynucleotide.

23. A vector comprising the polynucleotide of claim 1.

24. A vector comprising the polynucleotide of claim 9.

25. A vector comprising the polynucleotide of claim 16.

26. A host cell comprising the polynucleotide of claim 1 operably associated with a heterologous regulatory sequence.

27. A host cell comprising the polynucleotide of claim 9 operably associated with a heterologous regulatory sequence.

28. A host cell comprising the polynucleotide of claim 16 operably associated with a heterologous regulatory sequence.

29. A method of producing a polypeptide comprising:
   (a) culturing the host cell of claim 26 under conditions such that the polypeptide is expressed; and
   b) recovering said polypeptide.

30. A method of producing a polypeptide comprising:
   a) culturing the host cell of claim 27 under conditions such that the polypeptide is expressed; and
   (b) recovering said polypeptide.

31. A method of screening a ligand comprising:
   (a) obtaining a sample suspected of containing said ligand
   (b) contacting the sample with the host cell of claim 29, and
   (c) determining whether the ligand binds to a polypeptide expressed by the polynucleotide.

32. A method of screening a ligand comprising:
   (a) obtaining a sample suspected of containing said ligand,
   (b) contacting the sample with the host cell of claim 30, and
   (c) determining whether the ligand binds to a polypeptide expressed by the polynucleotide.

33. A composition comprising the isolated polynucleotide of claim 1.

34. A composition comprising the isolated polynucleotide of claim 9.

35. A composition comprising the isolated polynucleotide of claim 16.

* * * * *